United States Patent [19]

Clayman

[11] Patent Number: 4,676,243
[45] Date of Patent: Jun. 30, 1987

[54] AUTOMATED ANTERIOR CAPSULECTOMY INSTRUMENT

[75] Inventor: Henry Clayman, Miami, Fla.

[73] Assignee: Aldebaran XIII Consulting Company, Miami Shores, Fla.

[21] Appl. No.: 666,816

[22] Filed: Oct. 31, 1984

[51] Int. Cl.⁴ .............................................. A61B 17/32
[52] U.S. Cl. ..................................... 128/305; 30/155; 604/289
[58] Field of Search ............. 128/305, 314, 305.3, 128/307, 309, 310, 311, 313; 604/289; 30/151, 155

[56] References Cited

U.S. PATENT DOCUMENTS

| | | | |
|---|---|---|---|
| 2,541,246 | 2/1951 | Held | 128/305 |
| 4,137,920 | 2/1979 | Bonnet | 128/311 |
| 4,440,169 | 4/1984 | Schulman | 128/305 |

FOREIGN PATENT DOCUMENTS

| | | | |
|---|---|---|---|
| 2737014 | 3/1979 | Fed. Rep. of Germany | 128/311 |
| 548303 | 9/1956 | Italy | 128/305 |
| 759098 | 8/1980 | U.S.S.R. | 128/305 |
| 938977 | 7/1982 | U.S.S.R. | 128/305 |

Primary Examiner—Robert Peshock
Assistant Examiner—John G. Weiss
Attorney, Agent, or Firm—Cushman, Darby & Cushman

[57] ABSTRACT

A surgical instrument with a handpiece body adapted for manual manipulation, a hollow tube extending outward therefrom, and a rotating blade extending through the tube and out of the end thereof. The axis of rotation of the blade is displaced radially from the tube axis so that, when the blade is rotated 180° from the direction of displacement, the sharp, hooked end is within the region of extension of the tube and the patient is protected against inadvertent cutting of Descemet's Membrane or the iris.

3 Claims, 4 Drawing Figures

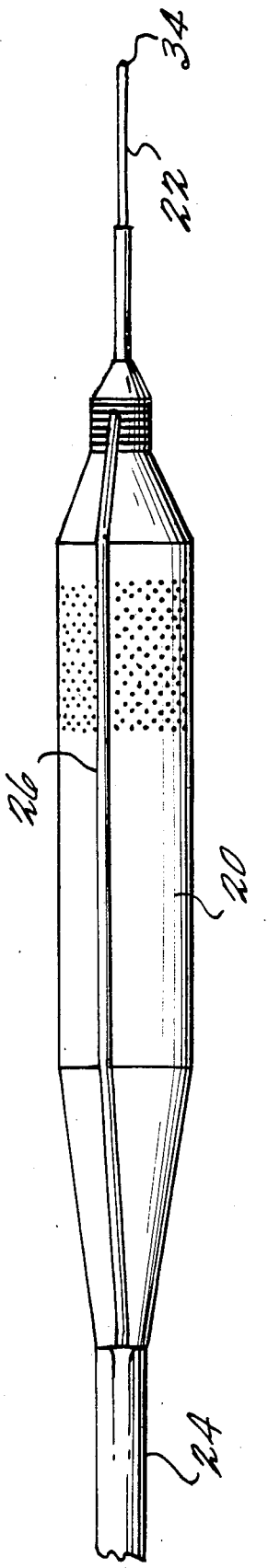
FIG. 1
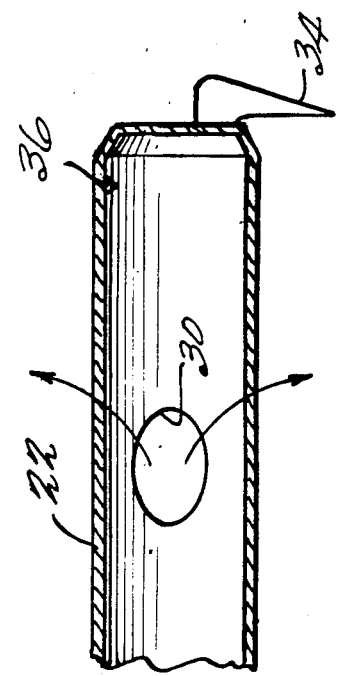
FIG. 2
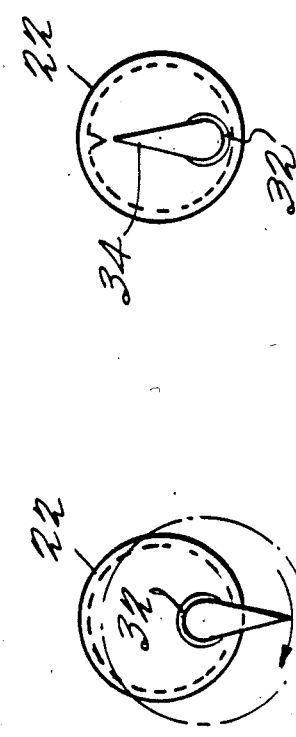
FIG. 3A
FIG. 3B

AUTOMATED ANTERIOR CAPSULECTOMY INSTRUMENT

BACKGROUND AND SUMMARY OF THE INVENTION

The invention relates to a surgical instrument and particularly an instrument for extracapsular cataract surgery.

With the advent of extracapsular cataract surgery, various methods have been advocated for anterior capsulectomy. These include non-invasive, manual and mechanical techniques. To date, no instrument has been developed for use with mechanical techniques in which a cutting blade or hook is inserted for cutting the anterior capsule. Vitrectomy instruments now in use are not suitable because the cutting mechanism is recessed within a hollow tube and cannot reach the capsule. The present invention is concerned with an instrument particularly useful in mechanical techniques.

One of the potential problems with mechanical techniques is the possibiliity inadvertent engagement of Descemet's Membrane or the iris of the eye.

The present invention relates to the first practical mechanical device in which the cutting blade extends beyond the end of a hollow tube. Moreover, the possibility of inadvertent engagement of Descemet's Membrane or the iris is substantially reduced by mounting a rotating blade in a hollow tube displaced radially from the axis of the hollow tube. The length of the tip distance of the displacement and circumference of the hollow tube are chosen so that, when the blade is rotated 180° from the direction of displacement, the hooked cutting tip is within the region of extension of the tube so that the tip is not readily exposed to these eye parts during incision. After incision, the tip is rotated to be aligned along the direction of displacement for cutting. The blade is coupled to a suitable drive controlled by surgeon in a conventional way.

Other objects and purposes of the invention will be clear from the following detailed description of the drawings.

BRIEF DESCRIPTION OF THE DRAWINGS

FIG. 1 shows a side view of the instrument of the present invention;

FIG. 2 shows a sectional view from the side of the end of the hollow tube and blade; and FIGS. 3A and 3B show end views of the instrument with the cutting blade respectively in the cutting and withdrawn positions.

DETAILED DESCRIPTION OF THE DRAWING

Reference is now made to FIG. 1 which shows a first embodiment of the present invention. Like vitrectomy instruments, a motor (not shown) is disposed within a handpiece body 20 from which a hollow tube 22 extends. Tube 22 may, for example, be a hollow 22 gauge tube, 30 mm in length. Cord 24 connects to a conventional battery power pack and to a conventional control circuit, some of the functions of which are described below. Hollow tube 22 also receives infusion fluid from line 26. As can be best seen in FIG. 2, infusion fluid escapes from the tube through two orifices near the end of hollow tube 22. One orifice 30 can be readily seen in FIG. 2, while the other orifice is directly behind that illustrated. Orifice 30 and the other hidden orifice are positioned such that flow is directed away from the cutting tip and underlying anterior capsule.

As can be best seen in FIGS. 3A and 3B, a rotating blade 32 is mounted within tube 22 with its axis of rotation displaced from the axis of tube 22 by a given distance. Therefore the hooked cutting tip 34 of blade 32 is exposed in the downward position where it cuts in the inferior (lower) 45° of its total 360 rotary motion. When the tip is rotated superiorly (to an upper position), as shown in FIG. 3B, its sharp point is within the extension of the tube and, therefore, in this withdrawn position there is no possibility of inadvertent engagement of any undesired eye parts.

The tip can be easily oriented by the surgeon, who simply rotates tip 34 until it coincides with a scribe mark 36 on tube 22. The surgeon can easily see through his microscope when cutting tip 34 and mark 36 are aligned. Alternatively, the infusion line groove on the hand probe can be utilized for orientation since it is aligned exactly 180° in opposition to the hooked blade's maximally exposed cutting position. Anterior chamber depth is maintained by infusion or by the use of viscoelastic space expanders, such as sodium hyaluronate.

The surgeon's food pedal (not shown) typically has two speeds. Half-depression rotates the blade slowly and allows the surgeon to position it superiorly in its withdrawn position for passage in and out of the incision. With full depression, the blade spins at 10,000–12,000 rpm and stops in 25 milliseconds by means of an electromagnetic brake, activated by foot pedal release.

Power is supplied by a low voltage battery, for example, six volts, which is enough to run the device continuously for up to six hours. An integrated circuit conventionally monitors the battery's charge and warns the surgeon with an audiovisual alarm when the charge has been 90% depleted. The probe is preferably heat autoclavable for sterilization and may be "flash sterilized" for rapid reuse.

Normally, the device will operate in a rotary mode to cut. However, an oscillatory mode can be obtained with some alternative power sources available in the market. Both modes have been used clinically and perform an adequate and expeditious capsulectomy without rocking the nucleus of the lens and without causing a zonular dialysis.

Many changes and modifications in the above-described embodiment of the invention can, of course, be carried out without departing from the scope thereof. Accordingly, that scope is intended to be limited only by the scope of the appended claims.

What is claimed is:
1. A surgical instrument comprising:
   a handpiece body adapted to be manually manipulated;
   a hollow tube extending distally from said body for insertion into the eye as said body is manually manipulated;
   a blade having a first portion mounted within said tube and a second portion terminating in a sharp tip and extending beyond a distal end of said tube at an angle relative to a longitudinal axis of said first portion; said first portion having an axis of rotation longitudinally oriented with respect to said hollow tube at a fixed longitudinal position and displaced radially in a first direction from the center axis of said hollow tube; the length of said second portion, the amount of displacement of said axis of rotation, and the diameter of said hollow tube being such that, when said sharp tip is rotated 180° with respect to said first direction, said sharp tip is within a region defined by extending said tube along said center axis and, when said tip is oriented in said first direction, said tip extends outside said region; and means within said body for rotating said blade.

2. An instrument as in claim 1 wherein said tube is provided with at least one aperture adjacent the end of said tube for supplying infusion fluid to the cutting site during surgery.

3. An instrument as in claim 1 wherein said tube is provided at said end with a scribe mark 180° from said first direction.

* * * * *